(12) United States Patent
Roh et al.

(10) Patent No.: US 10,500,069 B2
(45) Date of Patent: Dec. 10, 2019

(54) DRIVING MODULE AND MOTION ASSISTANCE APPARATUS INCLUDING THE SAME

(71) Applicant: Samsung Electronics Co., Ltd., Suwon-si, Gyeonggi-do (KR)

(72) Inventors: Se-Gon Roh, Suwon-si (KR); Youn Baek Lee, Yongin-si (KR); Byungjune Choi, Yongin-si (KR); Jeonghun Kim, Hwaseong-si (KR); ChangHyun Roh, Seongnam-si (KR); Youngjin Park, Seoul (KR); Minhyung Lee, Anyang-si (KR); Jongwon Lee, Suwon-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 720 days.

(21) Appl. No.: 15/074,041

(22) Filed: Mar. 18, 2016

(65) Prior Publication Data

US 2017/0128234 A1    May 11, 2017

(30) Foreign Application Priority Data

Nov. 5, 2015    (KR) .................. 10-2015-0155263

(51) Int. Cl.
*F16H 57/02*    (2012.01)
*A61F 2/60*    (2006.01)
(Continued)

(52) U.S. Cl.
CPC ............ *A61F 2/605* (2013.01); *A61F 5/0102* (2013.01); *F16H 57/0006* (2013.01);
(Continued)

(58) Field of Classification Search
CPC ... A61H 3/00; F16H 2057/02034; A61F 2/30; A61F 2/68
See application file for complete search history.

(56) References Cited

U.S. PATENT DOCUMENTS 7,404,782 B2 *  7/2008  Kudoh ................ A61H 1/0237
                                                 475/337
7,998,096 B1 *  8/2011  Skoog ..................... A61H 3/00
                                                 601/35
(Continued)

FOREIGN PATENT DOCUMENTS

JP    2004-089376    3/2004
JP    2009-178369    8/2009
(Continued)

OTHER PUBLICATIONS

Machine translation of KR20050099273 filed Oct. 1, 2018 (Year: 2018).*

*Primary Examiner* — Tisha D Lewis
(74) *Attorney, Agent, or Firm* — Harness, Dickey & Pierce, P.L.C.

(57) ABSTRACT

A driving module may include a driving source configured to generate power, a gear train that includes a decelerating gear set configured to receive driving power from the driving source and a ring gear attached to one side of the gear train, and a rotary joint that includes at least one planetary gear configured to rotate in response to power received from an output end of the decelerating gear set and to revolve along the ring gear. The driving module may include one or more noise reducing members configured to mitigate noise produced based on interaction between one or more elements of the driving module. The driving module may be included in a motion assistance apparatus, where the driving module drives a module that supports a portion of a user body.

19 Claims, 13 Drawing Sheets

(51) Int. Cl.
    *F16H 57/00*     (2012.01)
    *A61F 5/01*     (2006.01)
    *F16H 1/28*     (2006.01)
    *F16H 37/04*     (2006.01)
    *A61F 2/50*     (2006.01)

(52) U.S. Cl.
    CPC . *A61F 2002/5038* (2013.01); *A61F 2002/608* (2013.01); *A61F 2005/0155* (2013.01); *F16H 1/28* (2013.01); *F16H 37/041* (2013.01)

(56) References Cited

U.S. PATENT DOCUMENTS

| | | | | |
|---|---|---|---|---|
| 2002/0077708 | A1* | 6/2002 | Iversen | A61F 2/54 |
| | | | | 623/64 |
| 2009/0299480 | A1* | 12/2009 | Gilbert | A61F 2/582 |
| | | | | 623/18.11 |
| 2011/0066093 | A1* | 3/2011 | Vess | A61H 11/00 |
| | | | | 601/148 |
| 2016/0193102 | A1* | 7/2016 | Roh | A61H 3/00 |
| | | | | 623/27 |
| 2016/0317375 | A1* | 11/2016 | Simon | A61F 2/605 |

FOREIGN PATENT DOCUMENTS

| | | |
|---|---|---|
| JP | 2012-192013 | 10/2012 |
| JP | 2014-030338 | 2/2014 |
| KR | 10-2005-0099273 | 10/2005 |
| KR | 10-1392727 | 4/2013 |
| KR | 10-1488192 | 1/2015 |

\* cited by examiner

DRIVING MODULE AND MOTION ASSISTANCE APPARATUS INCLUDING THE SAME

CROSS-REFERENCE TO RELATED APPLICATION

This application claims under 35 U.S.C. § 119 to Korean Patent Application No. 10-2015-0155263, filed on Nov. 5, 2015, in the Korean Intellectual Property Office, the entire contents of which are incorporated herein by reference in its entirety.

BACKGROUND

1. Field

At least one example embodiment relates to a driving module and/or a motion assistance apparatus including the same.

2. Description of the Related Art

Biped walking may aid a human in performing various daily activities by freeing the hands of the human during walking. When experiencing difficulties in such significant walking, a human body may be exposed to a number of issues. For example, a decrease in muscular strength may restrict physical activities and cause a reduction in muscle mass, energy consumption, and metabolism.

Walking assistance robots/walking assistance devices are being developed to aid those people having difficulties in walking to be able to walk with less difficulty. Such robots/devices may be worn on/attached to a lower body of a user to intensify muscular strength and alleviate a burden by weight during standing or walking on a level ground, a slope, or stairs.

In general, the robots/devices may have a structure to assist motions of joints of a lower body, for example, hip joints, knee joints, and ankle joints using an actuator. In the past, such robots/devices were developed to assist walking/intensify muscular strength of a patient. However, recently, the robots/devices are being developed to improve walking abilities for military purposes, manufacturing purposes, and general walking assistance purposes.

For example, to transmit a force and a torque generated by the actuator to joints of a user, a wearable portion acting as an interface between joints of the user and the device may be provided to be attached to or to enclose a body of the user. When driving power is transmitted in a direction in which a joint portion of the device connected to the wearable portion matches a moving direction of the joint of the user, the force and the torque may be applied appropriately without causing inconvenience. A driving source may include a motor and a decelerator, and may be disposed at a position corresponding to a rotation axis of the joint of the user. The wearable portion may be provided in a form of a belt or a band so that a frame connected to the driving source may be attached to a leg portion of the user. Such a structure may be an external skeleton structure in which the driving source and the wearable portion are relatively thick, and may be worn over clothing to be exposed to an outside.

SUMMARY

According to some example embodiments, a driving module may include a driving source configured to generate power, a gear train having first and second sides, a rotary joint rotatably coupled to the second side of the gear train such that the rotary joint is configured to rotate based on rotation of the decelerating gear, and a ring between the frame set and the rotary joint, the ring being configured to at least partially mitigate noise produced based on interaction between the frame set and the rotary joint if the rotary joint rotates. The gear train may be connected to the driving source at the first side of the gear train. The gear train may include a frame set that includes at least one frame, and a decelerating gear set configured to rotate in response to the power generated by the driving source.

In some example embodiments, the gear train may include a ring gear, the decelerating gear set may include a plurality of gears, each gear of the plurality of gears including a separate shaft. The at least one frame may include a first frame that is integral with the shafts of the plurality of gears and a second frame coupled to the ring gear.

In some example embodiments, the decelerating gear set may include an input gear connected to a drive shaft of the driving source, an idle gear configured to engage with the input gear, and a base gear configured to engage with the idle gear. The input gear may have a first diameter, the idle gear may have a second diameter, and the base gear may have a third diameter. The second diameter may be greater than the first diameter according to an order of power transmission, and the third diameter may be greater than the second diameter according to the order of power transmission.

In some example embodiments, the rotary joint may include at least one planetary gear that has a shaft and a carrier formed integrally with the shaft of the planetary gear, where the carrier is configured to rotate based on the planetary gear engaging with the ring gear.

In some example embodiments, the base gear may include at least a first gear and a second gear, the second gear having a greater diameter than the first gear, and the first gear being configured to engage with the planetary gear.

In some example embodiments, the planetary gear may include a first planetary gear and a second planetary gear, the second planetary gear having a greater diameter than the first diameter, the first planetary gear and the second planetary gear are an integral body, the first planetary gear is configured to engage with the ring gear, and the second planetary gear is configured to engage with the first gear of the base gear.

In some example embodiments, the second gear of the base gear may include a high-strength plastic material, the first gear of the base gear may include a metallic material, and the first gear of the base gear may be coupled to an inner side of the second gear of the base gear.

In some example embodiments, the rotary joint may include an aligner configured to prevent a separation of the planetary gear, the aligner may be attached to the carrier, and the planetary gear may be between the rotary joint and the aligner.

In some example embodiments, the gear train may further include a plurality of pools on at least one of an inner side of the first frame and an inner side of the second frame. The plurality of pools may be configured to at least partially mitigate noise produced by the decelerating gear set.

In some example embodiments, the base gear may include a shaft, the gear train may include a base bearing and a base ring, the base bearing and the base ring being between the base gear and the shaft of the base gear, and the base ring may be spaced apart from the first frame such that the base ring is configured to isolate the base gear from the first frame.

In some example embodiments, the first frame may include a shaft, the gear train may include a plurality of base bearings and a plurality of base rings, the base bearings may be between the second gear of the base gear and the shaft of the first frame, and the base rings may be between the first gear of the base gear and the shaft of the first frame.

In some example embodiments, the gear train may further include a bottom ring between the first frame and the idle gear, an idle bearing, and a cap ring between the second frame and a shaft of the idle gear. The cap ring may be configured to separate the idle gear from the second frame to isolate the idle gear from the second frame.

In some example embodiments, the rotary joint may further include at least one planetary ring between the carrier and the planetary gear, the at least one planetary ring including a plastic material, the planetary ring being configured to at least partially mitigate noise produced based on interaction between the carrier and the planetary gear if the rotary joint rotates.

In some example embodiments, the driving module may include a magnetic direction shaft configured to extend through a shaft of the base gear and a center of the rotary joint.

According to some example embodiments, a driving module may include a driving source configured to generate power, a decelerating gear set configured to rotate in response to the power received from the driving source, the decelerating gear set including at least one spur gear, a first frame, a second frame, a ring gear, a planetary gear set, a carrier rotatably attached to the second frame, a decelerating gear bearing, and a planetary gear bearing. The first frame may include an outer side and an inner side, the outer side being coupled to the driving source, and a shaft of the decelerating gear set, the shaft of the decelerating gear set configured to be inserted into the decelerating gear set. The second frame may be coupled to the inner side of the first frame. The ring gear may be coupled to the second frame. The planetary gear set may be configured to engage with the ring gear, the planetary gear set including at least one planetary gear. The carrier may include a shaft of the planetary gear set, the shaft of the planetary gear set configured to be inserted into the planetary gear set. The decelerating gear bearing may be between the decelerating gear set and the shaft of the decelerating gear set. The planetary gear bearing may be between the planetary gear set and the shaft of the planetary gear set.

In some example embodiments, at least one of the first frame and the second frame includes a plurality of pools on an inner side thereof, such that the plurality of pools are configured to at least partially mitigate noise produced by the decelerating gear set. The driving module may further include at least one first ring between the decelerating gear bearing and the shaft of the carrier, at least one second ring between the planetary gear bearing and the carrier, and at least one of the first ring and the second ring includes a plastic material.

In some example embodiments, the driving module may include a joint bearing having an inner side and an outer side, the inner side being configured to contact the ring gear, the outer side being configured to contact the carrier, wherein the joint bearing is configured to rotatably couple the carrier to the second frame.

According to some example embodiments, a motion assistance apparatus includes a fixing module configured to be coupled to a user, a supporting module configured to support a portion of a body of the user, and a driving module configured to drive the supporting module. The driving module may include a driving source, a gear train configured to receive driving power from the driving source, the gear train including an output end, and a rotary joint that includes at least one planetary gear coupled to the output end of the gear train. The gear train may further include a noise reduction member configured to at least partially mitigate noise produced based on interaction between the gear train and the rotary joint if the rotary joint rotates.

In some example embodiments, the gear train may include a decelerating gear set configured to rotate in response to power received from the driving source and a planetary gear set configured to engage with the decelerating gear set and of which a shaft is formed in the rotary joint. The noise reduction member may include at least one ring on a shaft of at least one of the decelerating gear set and the shaft of the planetary gear set.

In some example embodiments, the gear train may include at least one frame that is integral with the shaft of the decelerating gear, and the noise reduction member may include a plurality of pools on an inner side of the at least one frame.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
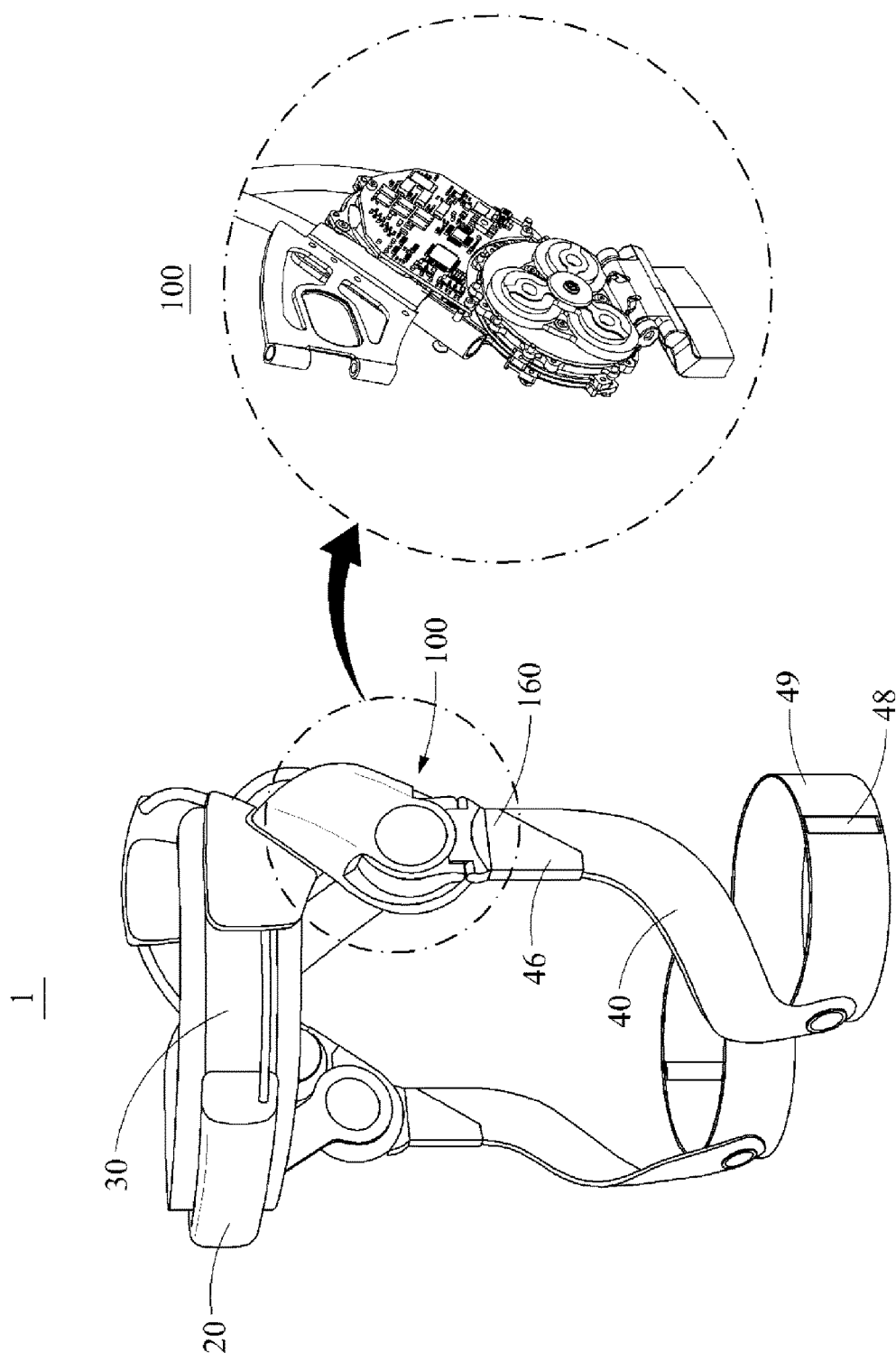
FIG. 1 is a perspective view illustrating a motion assistance apparatus including a driving module according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

FIG. 1 illustrates a motion assistance apparatus and a driving module according to at least one example embodiment.

Referring to FIG. 1, a motion assistance apparatus 1 may be worn by a user to assist a motion of the user.

The user may be, for example, a human, an animal, or a robot. However, example embodiments are not limited thereto. Although FIG. 1 illustrates a case in which the motion assistance apparatus 1 assists a motion of a thigh of the user, the motion assistance apparatus 1 may assist a motion of another part of an upper body, for example, a hand, an upper arm, and a lower arm of the user, or a motion of another part of a lower body, for example, a foot, and a calf of the user. Thus, the motion assistance apparatus 1 may assist a motion of a part of the user.

To distribute a motion assistance apparatus in a daily life, the motion assistance apparatus may transmit driving power as an assistance device, a volume of the motion assistance apparatus is to decease, and an inconvenience cause by a contact with a human body is to be minimized. Further, the motion assistance apparatus is to be worn under clothing not to be exposed to an outside.

Conventionally, a motion assistance apparatus is capable of performing a functional role. Conventionally, a motion assistance apparatus may protrude and stick out due to a motor and a decelerator disposed in an axial direction at positions corresponding to joints. Thus, the motion assistance apparatus may not be hidden under pants, and the entire structure thereof may be exposed to an outside.

The motion assistance apparatus according to at least one example embodiment may enable components to be disposed at a joint all together, minimize a protruding height of a structure to be worn at a lower body of a user, and include a slim joint-integrated driving module. Through the foregoing, the motion assistance apparatus may be light-weighted through a slim appearance and structure optimization, have improved wearability, and transmit driving power effectively.

A driving module according to at least one example embodiment includes an improved gear structure and joint arrangement, and uses a light-weighted and slim structure. Thus, it may be difficult to prevent noise produced during an operation. Accordingly, the driving module may include a structure for preventing or restraining noise production and a mechanism for reducing noise.

The motion assistance apparatus 1 may include a fixing module 30, a supporting module 40, a driving module 100, and a controller 20 configured to control the driving module 100.

The controller 20 may include a memory and a processor (not shown). In some example embodiments, the controller 20 may include a computer processing device.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform one or more operations, including controlling the driving module 100. Controlling the driving module 100 may include performing feed forward control by modifying a walking assist profile to increase or decrease an assistance torque applied by the driving module 100 to the right leg and the left leg of the user based on whether a joint angle indicates that the user is performing positive or negative work thereon. Therefore the processor may improve the functioning of the controller 20 itself by modifying the walking assist profile to perform the natural gait assistance when the gait style of the user suddenly changes.

Figure 2:
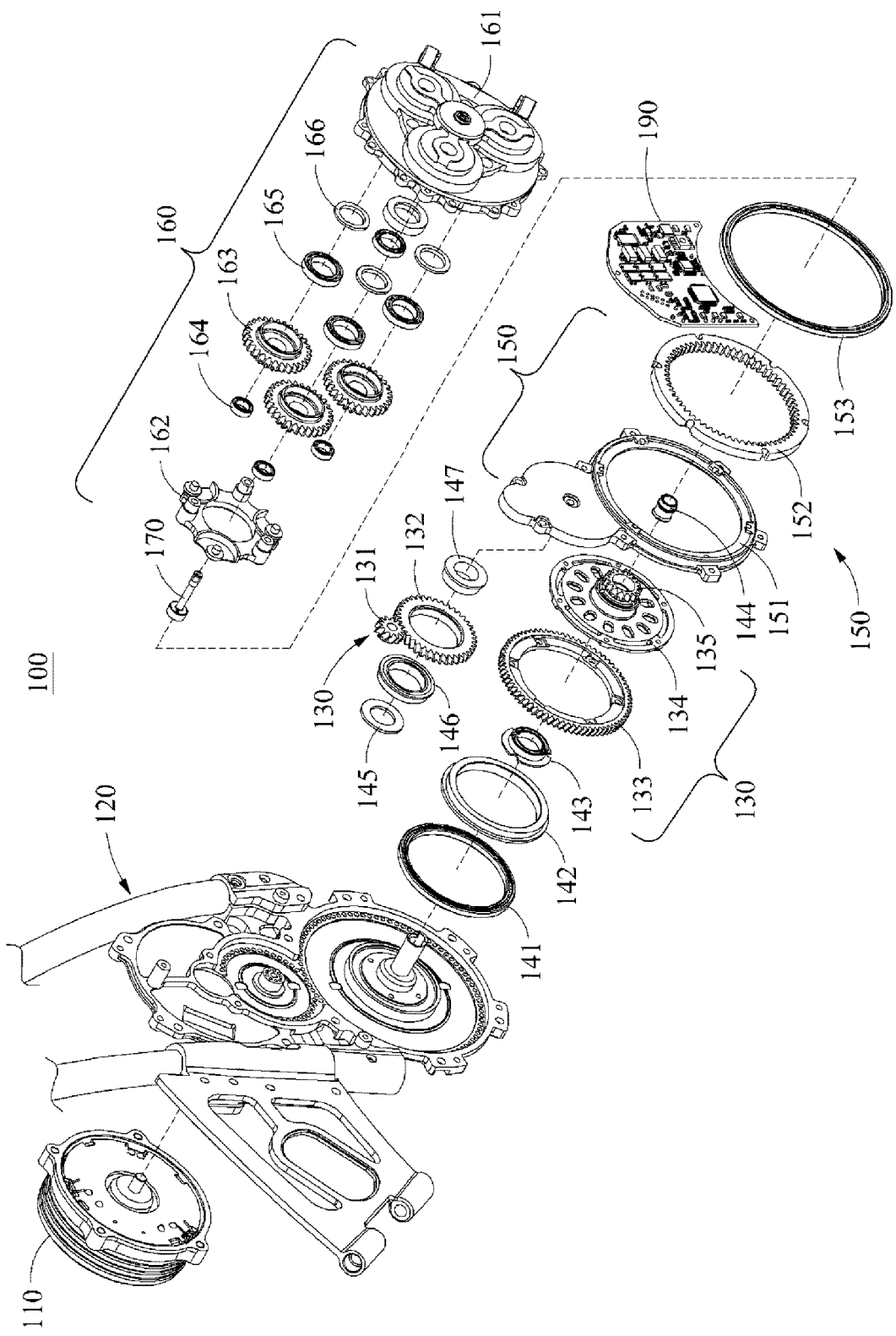
FIGS. 2 and 3 are exploded perspective views illustrating a driving module according to at least one example embodiment.
Figure 3:
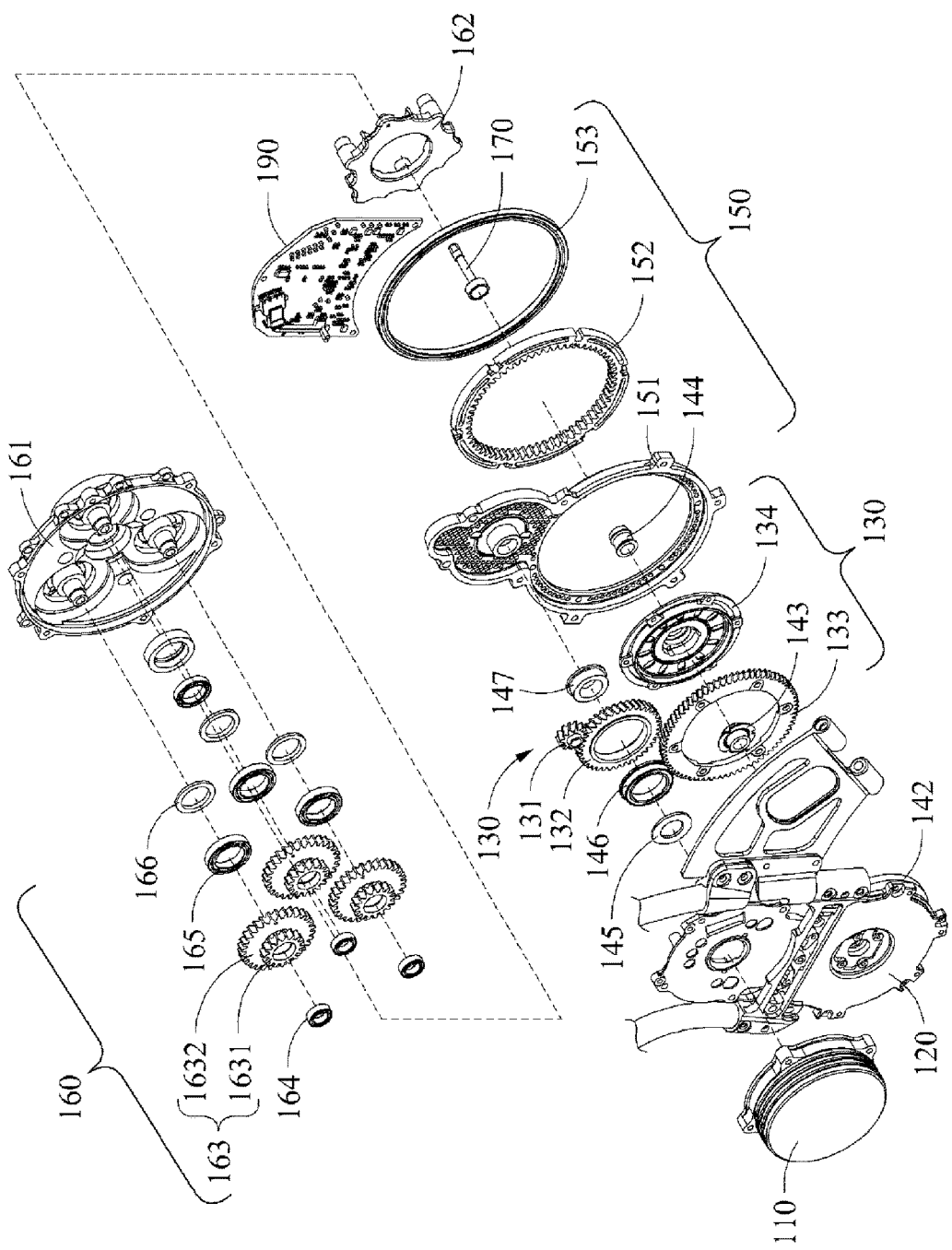

Referring to FIG. 2 and FIG. 3, the driving module 100 may include a driving source 110 disposed on one side of the fixing module 30, a gear train configured to receive driving power from the driving source 110, and a rotary joint 160 including at least one planetary gear connected to an output end of the gear train. A connecting member may be connected to the rotary joint 160. The driving module 100 may be disposed on a hip joint of a user to drive a joint portion of the motion assistance apparatus 1. Two driving modules 100 may be disposed on left and right hip joints of the user to assist rotary motions of the left and right hip joints, respectively. The driving module 100 will be described in detail later.

Returning to FIG. 1, the fixing module 30 may be attached to the user. The fixing module 30 may touch at least a portion of an outer surface of the user, and may be provided to cover the outer surface of the user. The fixing module 30 may include a curved surface to be in contact with the user. For example, the fixing module 30 may be attached to one side of a waist of the user.

The supporting module 40 may include a supporting frame 46. The supporting frame 46 coupled to the connecting member may rotate in a direction in which the connecting member is rotated by the driving module 100. The supporting module 40 may further include a pressurizing member 48 connected from the supporting frame 46, and a supporting member 49.

The pressurizing member 48 may be connected to one side of the supporting frame 46. For example, the pressurizing member 48 may be disposed on one side of a leg of the user to pull or push a thigh of the user. The pressurizing member 48 may be disposed on a front surface of the thigh of the user.

The supporting member 49 may be connected to one side of the pressurizing member 48. For example, the supporting member 49 may be disposed to cover a circumference of at least a portion of the thigh of the user, thereby preventing a separation of the thigh of the user from the supporting frame 46. The supporting member 49 may be disposed on an opposite side of the pressurizing member 48 from the thigh of the user.

A torque generated by the driving module 100 may be transmitted to the supporting module 40 through the connecting member. The torque transmitted through the supporting module 40 may be used to lift the thigh of the user through the pressurizing member 48, thereby assisting a motion of the user.

FIG. 2 is an exploded perspective view illustrating the driving module 100 according to at least one example embodiment, and FIG. 3 is an exploded perspective view illustrating the driving module 100 of FIG. 2, viewed from another angle. In detail, FIG. 2 is an exploded perspective view of the driving module 100 viewed from the rotary joint 160, and FIG. 3 is an exploded perspective view of the driving module 100 viewed from the driving source 110.

Conventionally, a driving module may be restricted from inhibiting noise produced by gear teeth engagement/bump/friction occurring in response to gear rotation with a high gear ratio due to a thin thickness of a body frame of the driving module. Rather, the thin frame may resonate and thereby amplify the noise.

In a case in which a frame set is provided in an extremely slim structure, additional noise, which may not be produced in a frame with a desired (or, alternatively, predetermined) thickness, for example, a 2 to 3-millimeter thickness, may be produced. When a frame is thin, the frame may have a low rigidity and thus, oscillation and noise may be produced by gear engagement, oscillation may be produced when a ball of a bearing disposed in a gear rolls, and noise may be produced by friction between the ball and a bearing housing, which may generate frictional sounds like scratching frame sets. Such frictional sounds are high frequency sounds that are harsh to ears of a user. In addition, such sounds are transmitted to the frame, and the frame oscillates and resonates.

Noise produced by gear engagement and noise produced by shaking of a frame set are unique noise excluding that of a driving motor. The driving module 100 set forth hereinafter suggests various solutions for reducing noise.

Referring to FIG. 2 and FIG. 3, the driving module 100 may include the driving source 110 configured to generate power, the gear train including a frame set that includes at least one frame, in detail, a first frame 120 and a second frame 151, and a decelerating gear set 130 configured to rotate in response to the power received from the driving source 110, the driving source 110 being connected to one side of the decelerating gear set 130, the rotary joint 160 rotatably attached to the frame set, and at least one noise reduction member disposed in the frame set and the rotary joint 160 to reduce noise produced when the rotary joint 160 rotates. In some example embodiments, the at least one noise reduction member includes the sun ring 144.

The driving source 110 may generate power to be used to drive the rotary joint 160. The driving source 110 may be disposed, for example, in a space between a thigh and a hip of the user. The driving source 110 may be, for example, an electric motor. However, the type of the driving source 110 is not limited thereto.

The gear train may include a ring gear 152. The frame set may include the first frame 120 formed integrally with shafts of a plurality of gears included in the decelerating gear set 130, and the second frame 151 to which the ring gear 152 is attached.

When the respective shafts of decelerating gears constituting the decelerating gear set 130 are provided integrally with the first frame 120, an additional component and a space to fix the shafts of the decelerating gears to the first frame 120 may be absent. Thus, the size of the gear train may be minimized.

The decelerating gears of the decelerating gear set 130 may include an input gear 131 connected to a drive shaft of the driving source 110, an idle gear 132 configured to engage with the input gear 131, and a base gear configured to engage with the idle gear 132. Diameters of the input gear 131, the idle gear 132, and the base gear may increase sequentially in an order of power transmission. For example, the input gear may have a first diameter, the idle gear may have a second diameter, and the base gear may have a third diameter. The second diameter may be greater than the first diameter according to an order of power transmission. The third diameter may be greater than the second diameter according to an order of power transmission.

The decelerating gear set 130 may decrease a rotation velocity of a rotary motion transmitted from the driving module 100 and generate a relatively great torque. The decelerating gear set 130 may include, for example, spur gears or helical gears. A gear acting as an output end of the decelerating gear set 130 may be referred to as the base gear.

The base gear may include two gears having different diameters, and a connecting plate 134 configured to couple the two gears together. Between the two gears of the base gear a small-diameter gear (also referred to herein as a "first gear" of the base gear) 135 may act as a sun gear configured to engage with a planetary gear 163, and a large-diameter gear (also referred to herein as a "second gear" of the base gear) 133 may engage with the idle gear 132. Hereinafter, the small-diameter gear 135 may also be referred to as the sun gear 135.

The torque generated by the driving source 110 may be transmitted sequentially to the input gear 131, the idle gear 132, and the base gear of the decelerating gear set 130. The base gear is an integrated gear including the large-diameter gear 133 and the small-diameter gear 135 which are coaxial gears. Thus, the final torque of the decelerating gear set 130 may be transmitted to the sun gear 135 that is the small-diameter gear 135.

A bottom ring 145 and an idle bearing 146 may be disposed sequentially from the first frame 120 between the idle gear 132 and a shaft of the idle gear 132. A cap ring 147 may be disposed on a top of the idle gear 132. One end of the cap ring 147 may be inserted into the idle bearing 146 and touch the shaft of the idle gear 132 in the first frame 120, and another end of the cap ring 147 may cover the idle gear 132. The bottom ring 145, the idle bearing 146, and the cap ring 147 may be disposed to be concentric to the idle gear 132.

A shaft of the base gear in the first frame 120 may support an inner side of the base gear. The shaft of the base gear may include a first shaft with a large diameter and a second shaft with a small diameter. The second shaft may penetrate through an inner side of the sun gear 135. The first shaft and the second shaft may be disposed sequentially from the first frame 120.

A base ring 142 and a base bearing 141 may be disposed between the base gear and the first shaft of the base gear sequentially from the first frame 120. An auxiliary bearing assembly 143 and a sun ring 144 may be disposed between the sun gear 135 of the base gear and the second shaft of the base gear. A thin section bearing may be used for the base bearing 141.

The first frame 120 may be provided in a shape similar to the number "8" corresponding to the shape of the decelerating gears of the decelerating gear set 130. The size of the first frame 120 may increase toward a lower side thereof, and the first frame 120 may include an edge along an outer side of the first frame 120 to accommodate thicknesses of the decelerating gears of the decelerating gear set 130. For example, the first frame 120 may be provided in a shape of a thin plate in which a small-sized circle, a medium-sized circle overlapping a portion of the small-sized circle, and a large-sized circle overlapping a portion of the medium-sized circle are arranged sequentially.

A portion extending from the first frame 120 may be provided additionally at an upper end of a portion in which the input gear 131 is disposed in the first frame 120 so that a circuit board 190 configured to control the driving module 100 may be disposed in the extending portion.

The second frame 151 may be provided in a shape corresponding to the shape of the first frame 120. The second frame 151 may include a hollow on a lower side thereof to receive the ring gear 152. An inner side of the second frame 151 may cover the decelerating gear set 130 and be coupled to the first frame 120. The ring gear 152 may be attached to an outer side of the second frame 151. The second frame 151 may also include an edge along the outer side of the second frame 151 to accommodate the thicknesses of the decelerating gears of the decelerating gear set 130.

Based on a thickness direction of the ring gear 152, a portion of an inner side of the ring gear 152 may be inserted into the hollow of the second frame 151, and attached to the second frame 151 by bolt coupling. A joint bearing 153 may be disposed on an outer side of the ring gear 152. The ring gear 152 may be immovable when attached to the second frame 151.

The joint bearing 153 may have a larger diameter than the ring gear 152, and be firmly attached to the ring gear 152 along an outer circumference of the ring gear 152. Thus, the entire inner circumferential side of the joint bearing 153 may overlap a portion of an outer circumferential side of the ring gear 152. Once the joint bearing 153 is coupled to the ring gear 152, the joint bearing 153 may be firmly coupled to the ring gear 152 and may not be easily detached unless undergoing a desired (or, alternatively, predetermined) process. A thin section bearing may be used for the joint bearing 153.

Bolt holes may be provided along contours of the first frame 120 and the second frame 151 to couple the first frame 120 and the second frame 151 together.

The rotary joint 160 may be rotatably coupled to the ouster side of the second frame 151 by the joint bearing 153. The rotary joint 160 may include at least one planetary gear 163, and a carrier 161 formed integrally with the shaft of the planetary gear 163. Since the planetary gear 163 engages with both the ring gear 152 and the sun gear 135, the carrier 161 may rotate when the sun gear 135 rotates.

The rotary joint 160 may further include an aligner 162 configured to prevent a separation of the planetary gear 163. The aligner 162 may be coupled to an inner side of the carrier 161 while the planetary gear 163 is disposed therebetween. The aligner 162 and the carrier 160 may be fastened together using bolts inserted from an outer side of the carrier 161.

A planetary bearing 165 may be disposed between the planetary gear 163 and the shaft of the planetary gear 163. A batch bearing 164 may be disposed between the shaft of the planetary gear 163 and the aligner 162 to prevent shaking of the planetary gear 163. Further, at least one planetary ring 166 may be disposed between the carrier 161 and the planetary gear 163 to reduce frictional sounds between the planetary gear 163 and the sun gear 135 and resonance sounds transmitted to the carrier 161.

The planetary gear 163 may include a first planetary gear 1631 with a small diameter, and a second planetary gear 1632 with a large diameter. The first planetary gear 1631 and the second planetary gear 1632 may be formed as an integral body. The first planetary gear 1631 may engage with the ring gear 152, and the second planetary gear 1632 may engage with the sun gear 135.

The driving module 100 may further include a magnetic direction shaft 170 configured to penetrate through the shaft of the base gear and a center of the rotary joint 160.

Figure 4:
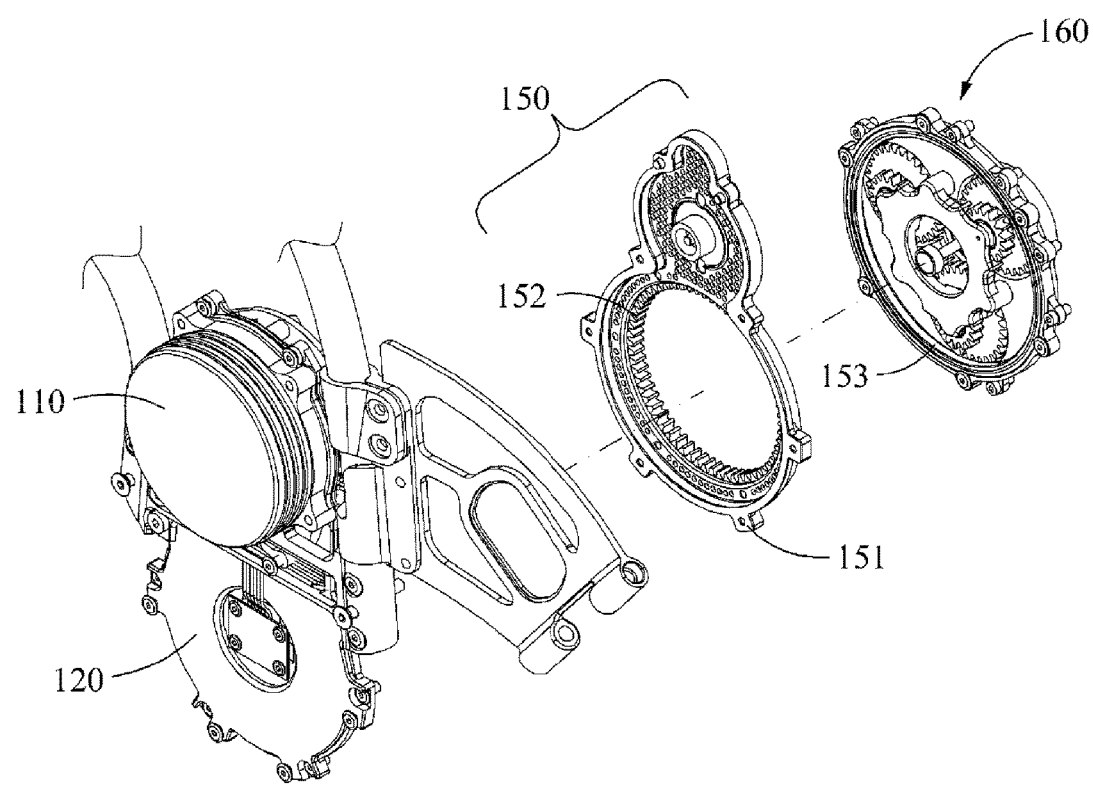
FIGS. 4 and 5 are partially exploded perspective views illustrating a driving module according to at least one example embodiment.
Figure 5:
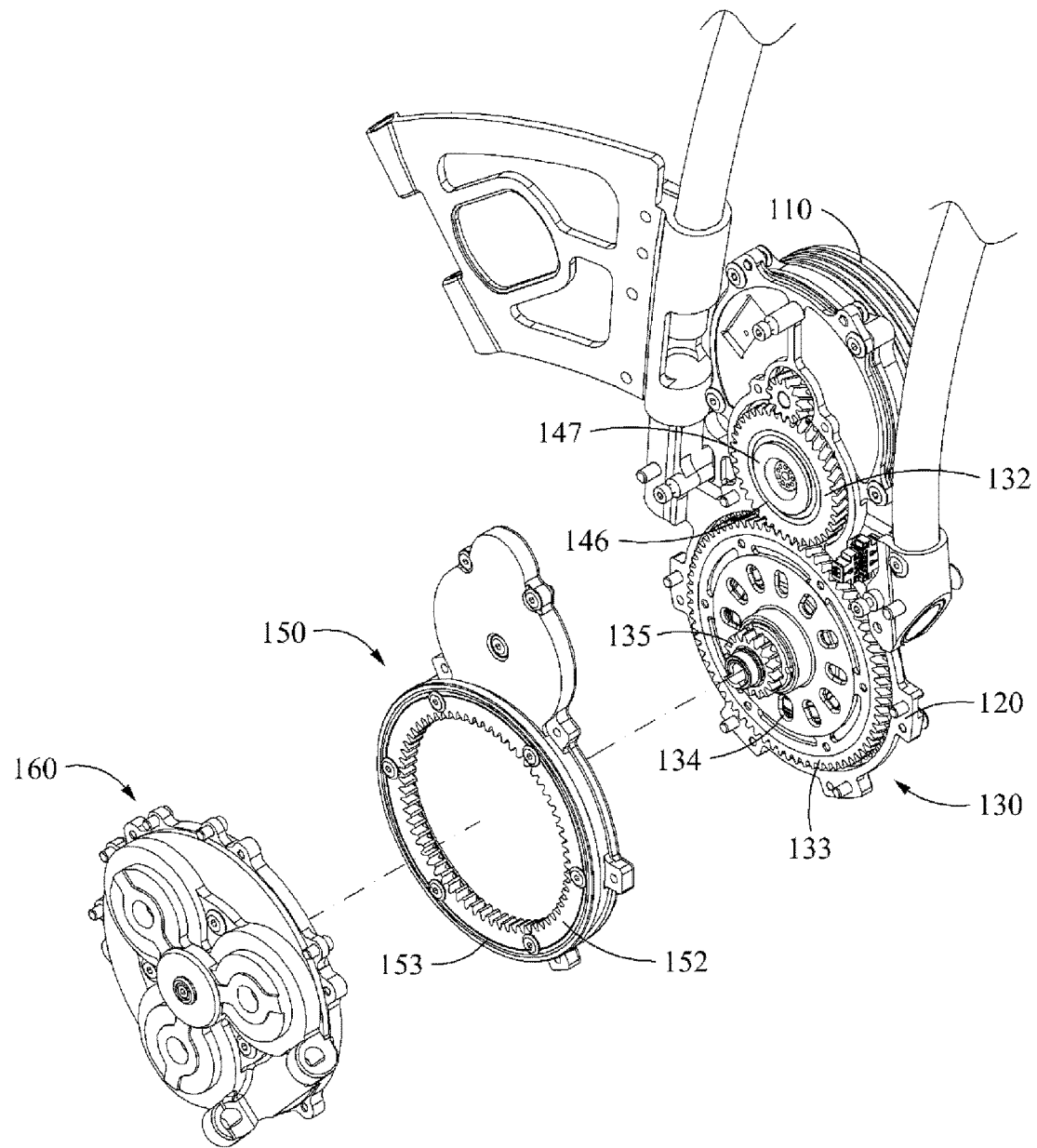

FIG. 4 and FIG. 5 are views illustrating the parts constituting the driving module 100 being partially assembled. FIG. 4 is an exploded perspective view of the driving module 100 viewed from the driving source 110, and FIG. 5 is an exploded perspective view of the driving module 100 viewed from the rotary joint 160.

Referring to FIG. 4, the driving source 110 may be coupled to a rear side of the first frame 120. A part to be connected to the fixing module 30 of the motion assistance apparatus 1 may be coupled to the rear side of the first frame 120. The part and the rear side of the first frame 120 may be firmly fastened together using bolts.

A second frame assembly 150 may be coupled to a front side of the first frame 120. The second frame 151 and the ring gear 152 may be disposed sequentially in the second frame assembly 150, and strongly coupled not to be detached from each other. Further, a shaft penetrating through a center of the idle gear 132 may be formed in the second frame 151.

Shafts of the idle gear 132 may be formed integrally (i.e., "is integral with") with the first frame 120 and the second frame 151, respectively. A diameter of the shaft of the idle gear 132 in the first frame 120 may be smaller than a diameter of the shaft of the idle gear 132 in the second frame 151. The shaft of the idle gear 132 in the first frame 120 may be inserted into a hollow of the shaft of the idle gear 132 in the second frame 151.

The cap ring 147 may be attached to the shaft of the idle gear 132 in the second frame 151. The idle bearing 146 and the idle gear 132 may be sequentially attached to the cap ring 147. Thus, an inner side of the cap ring 147 may touch the shaft of the idle gear 132 in the second frame 151, and an outer side of the cap ring 147 may touch an inner side of the idle bearing 146.

The base gear of the decelerating gear set 130 may be firmly attached to the shaft of the base gear in the first frame 120. Although heights of the other gears of the decelerating gear set 130 excluding the sun gear 135 may not exceed a height of the edge formed in the first frame 120, the sun gear 135 may protrude to a depth of the carrier 161 of the rotary joint 160 to be coupled to the planetary gear 163.

Referring to FIGS. 4 and 5, the joint bearing 153 may be attached to the outer circumferential side of the ring gear 152. A portion of the ring gear 152 may be inserted into the hollow of the second frame 151, and the joint bearing 153 may be attached to a remaining portion of the ring gear 152.

Further, an outer circumferential side of the joint bearing 153 may touch an inner side of the edge of the carrier 161, and an inner circumferential side of the joint bearing 153 may touch the outer side of the ring gear 152.

Figure 6:
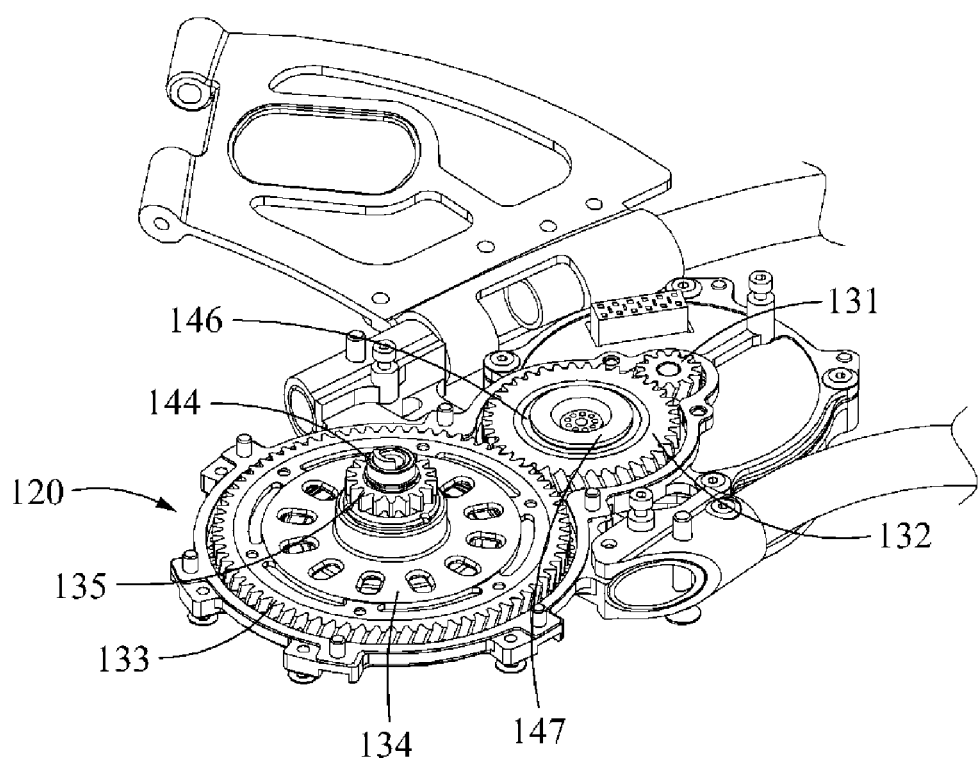
FIG. 6 is a perspective view illustrating a decelerating gear set of a driving module according to at least one example embodiment.

FIG. 6 illustrates the decelerating gear 130 of the driving module 100 being coupled to the first frame 120. The input gear 131 may be connected directly to the drive shaft of the driving source 110 and thus, a bearing may not be disposed in the input gear 131.

Referring to FIG. 6, the input gear 131 may engage with the idle gear 132. The cap ring 147 may be disposed around the shaft of the idle gear 132 in the first frame 120. The idle bearing 146 may be disposed under the cap ring 147.

The idle gear 132 may be coupled to the large-diameter gear 133 of the base gear, and the shaft of the base gear in the first frame 120 may extend to exceed a portion of the height of the sun gear 135 in a direction of the shaft of the base gear. The sun ring 144 may be disposed between the sun gear 135 and the shaft of the base gear, and the sun ring 144 may protrude more than the sun gear 135 in the direction of the shaft of the base gear.

All of the input gear 131, the idle gear 132, and the large-diameter gear 133 of the base gear may include a polyether ether ketone (PEEK) plastic material or engineering plastic material. The PEEK plastic material or engineering plastic material may at least partially mitigate noise produced when gear teeth bump each other (i.e., "interact"). Since the PEEK plastic material or engineering plastic material is lighter than a steel or aluminum material, the weight of the decelerating gear set 130 may be reduced.

Figure 7:
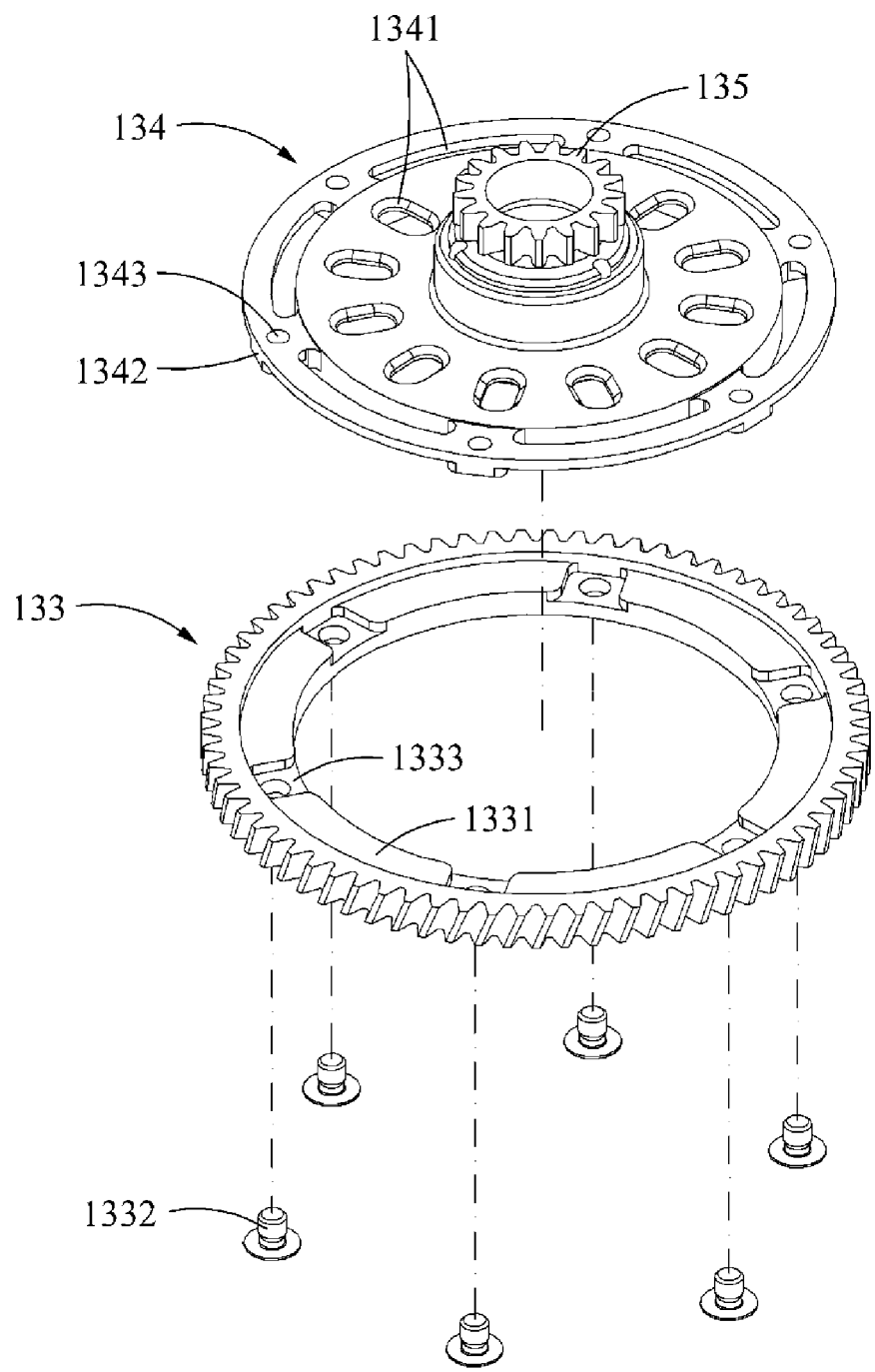
FIG. 7 is an exploded perspective view illustrating a base gear of a decelerating gear set according to at least one example embodiment.

FIG. 7 illustrates the base gear of the decelerating gear set 130. Referring to FIG. 7, the base gear may include the large-diameter gear 133 configured to engage with the idle gear 132 and act as a driven gear, the connecting plate 134, and the small-diameter gear 135 configured to act as a sun gear.

The connecting plate 134 and the sun gear 135 may be formed using the same material, and provided as an integral body. The sun gear 135 may transmit a strong torque to the rotary joint 160. The sun gear 135 may be formed using an A7075 aluminum material called super ultra duralumin. The A7075 aluminum material is a material with the greatest strength among aluminum alloys. Thus, the gear teeth may not be damaged although used for a long time, whereby the durability of the sun gear 135 may increase.

To change high-frequency noise to low-frequency noise, the base gear having a high linear velocity may be formed using two materials by selecting a PEEK plastic material plastic material rather than a metallic material as a material of the large-diameter gear 133 of the base gear, and selecting an aluminum material as a material of the sun gear 135 disposed at a center of the base gear. A portion of noise produced by gear bump may be primarily absorbed at a portion in which the connecting plate 134 and the large-diameter gear 133 are connected, and a level of the produced noise may be changed from a high-frequency band to a low-frequency band.

The large-diameter gear 133 may include an inner side 1331 configured to extend toward a center of the large-diameter gear 133. Coupling rods 1332 to be inserted in a thickness direction of the large-diameter gear 133 may be disposed on the inner side 1331 at desired (or, alternatively, predetermined) intervals along the circumference of the large-diameter gear 133. Coupling recesses 1333 dent toward the bottom of the inner side 1331 may be formed in vicinities of the coupling rods 1332 to secure spaces into which the coupling rods 1332 are to be inserted. Rod holes may be formed at central portions of the coupling recesses 1333 so that the coupling rods 1332 may be inserted from the bottom of the large-diameter gear 133.

Coupling holes 1343 may be disposed on an outer circumferential side of the connecting plate 134 in a circumferential direction of the connecting plate 134 so that the coupling rods 1332 may penetrate through the coupling holes 1343. Connecting protrusions 1342 to be inserted into the coupling recesses 1333 may be formed on the bottom of the connecting plate 134 in which the coupling holes 1343 are disposed.

When the connecting plate 134 is coupled to the large-diameter gear 133, the coupling rods 1332 may be inserted into the coupling holes 1343, and the connecting protrusions 1342 may be inserted into the coupling recesses 1333 at the same time such that a portion of the connecting plate 134 is inserted into a portion of the large-diameter gear 133, and a portion of the large-diameter gear 133 is also inserted into the connecting plate 134. Thus, the connecting plate 134 and the large-diameter gear 133 may be coupled to engage with each other, thereby being firmly coupled together without forming a gap therebetween.

Such a coupling method may solve a torsion occurring in a coupling space and a reduction in the durability caused by friction of each part, and may couple two gears together without using an adhesive.

The connecting plate 134 may include a plurality of holes 1341 disposed in a circumferential direction of the connecting plate 134. Since a metallic material is used for the connecting plate 134, the weight of the connecting plate 134 may increase. However, by disposing the holes 1341 in the connecting plate 134, the weight of the connecting plate 134 may be reduced, and a torsional rigidity of the connecting plate 134 may increase since a body with a hollow has a relatively great torsional rigidity when compared to a whole-connected continuum.

Figure 8A:
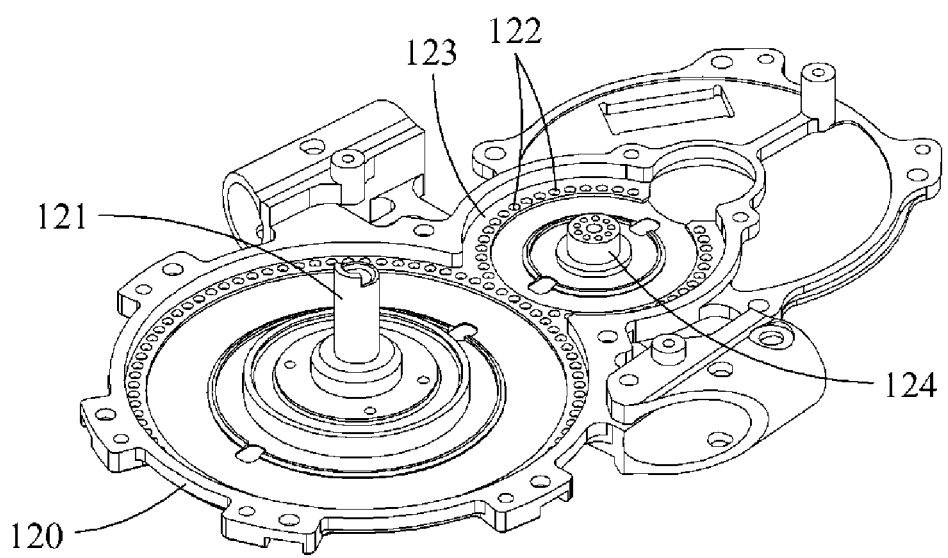
FIGS. 8A and 8B are perspective views illustrating a frame set of a driving module according to at least one example embodiment.
Figure 8B:
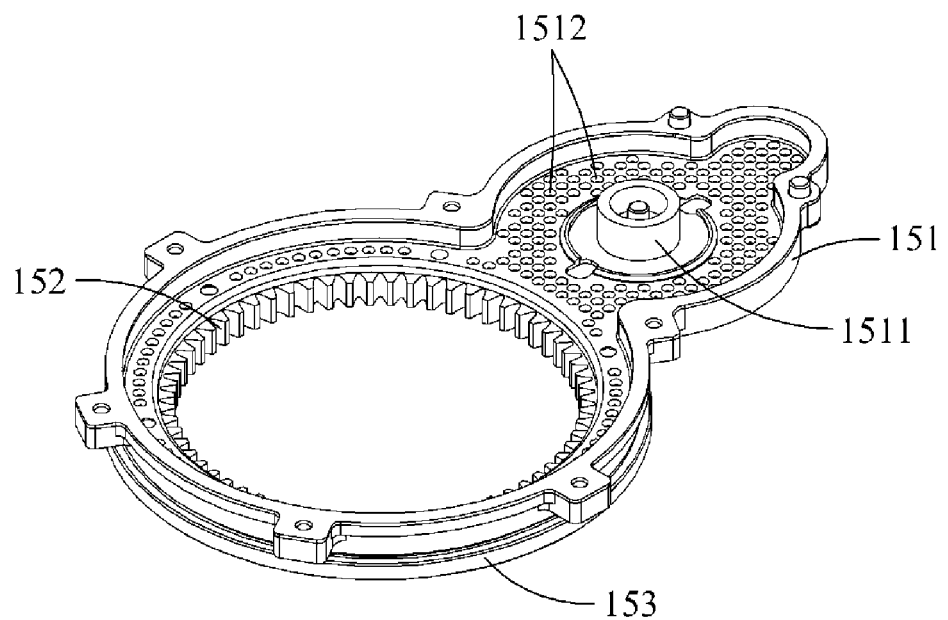

FIG. 8A and FIG. 8B illustrate the frame set including the first frame 120 and the second frame 151.

Referring to FIG. 8A and FIG. 8B, the first frame 120 may include a shaft 121 of the base gear formed in a lower portion of the first frame 120, and a shaft 124 of the idle gear 132 formed in an upper portion of the first frame 120. The shaft 121 of the base gear may be provided in a shape in which three cylinders having different diameters are coupled together, and the diameters of the cylinders decrease sequentially, starting from a cylinder close to the bottom of the first frame 120.

The first frame 120 may further include a bottom plate 123 provided around the shaft 121 of the base gear and the shaft 124 of the idle gear 132. A plurality of pools 122 may be provided in the bottom plate 123. Further, the second frame 151 may include a plurality of pools 1512 distributed on the entire inner side of the second frame 151. The plurality of pools 122 and 1512 may absorb noise produced when the decelerating gear set 130 rotates, or may prevent noise from being exposed to the outside of the frame set.

By disposing the plurality of pools 122 and 1512 on one side of the first frame 120 and one side of the second frame 151, respectively, the rigidness of the first frame 120 and the rigidness of the second frame 151 may increase, and noise produced when the decelerating gear set 130 rotates may be reduced at the same time.

The plurality of pools 122 and 1512 may be provided in a hemispherical shape, and the hemispherical pools 122 and 1512 may be filled with grease. The grease may be uniformly sprayed onto the decelerating gears of the decelerating gear set 130 when the decelerating gear set 130 rotates, thereby at least partially mitigating noise produced by friction of the decelerating gears (i.e., noise produced based on interaction between the decelerating gears). The noise may be additionally absorbed due to a characteristic of the grease in the pools 122 and 1512.

The second frame 151 may include a shaft 1511 of the idle gear 132 formed in an upper portion of the inner side of the second frame 151. The shaft 1511 of the idle gear 132 in the second frame 151 may be connected to the shaft 124 of the idle gear 132 in the first frame 120. When the first frame 120 and the second frame 151 are coupled together, the shafts 124 and 1511 may be coupled to engage with each other.

The ring gear 152 may be coupled to an outer side of the second frame 151, and the joint bearing 153 may be coupled to an outer side of the ring gear 152. The edge formed along the contour of the second frame 151 may be smaller than the edge formed along the contour of the first frame 120. Thus, when viewed from the outside of the second frame 151, the first frame 120 and the second frame 151 may be coupled to each other in a form in which the second frame 151 covers the first frame 120.

Figure 9:
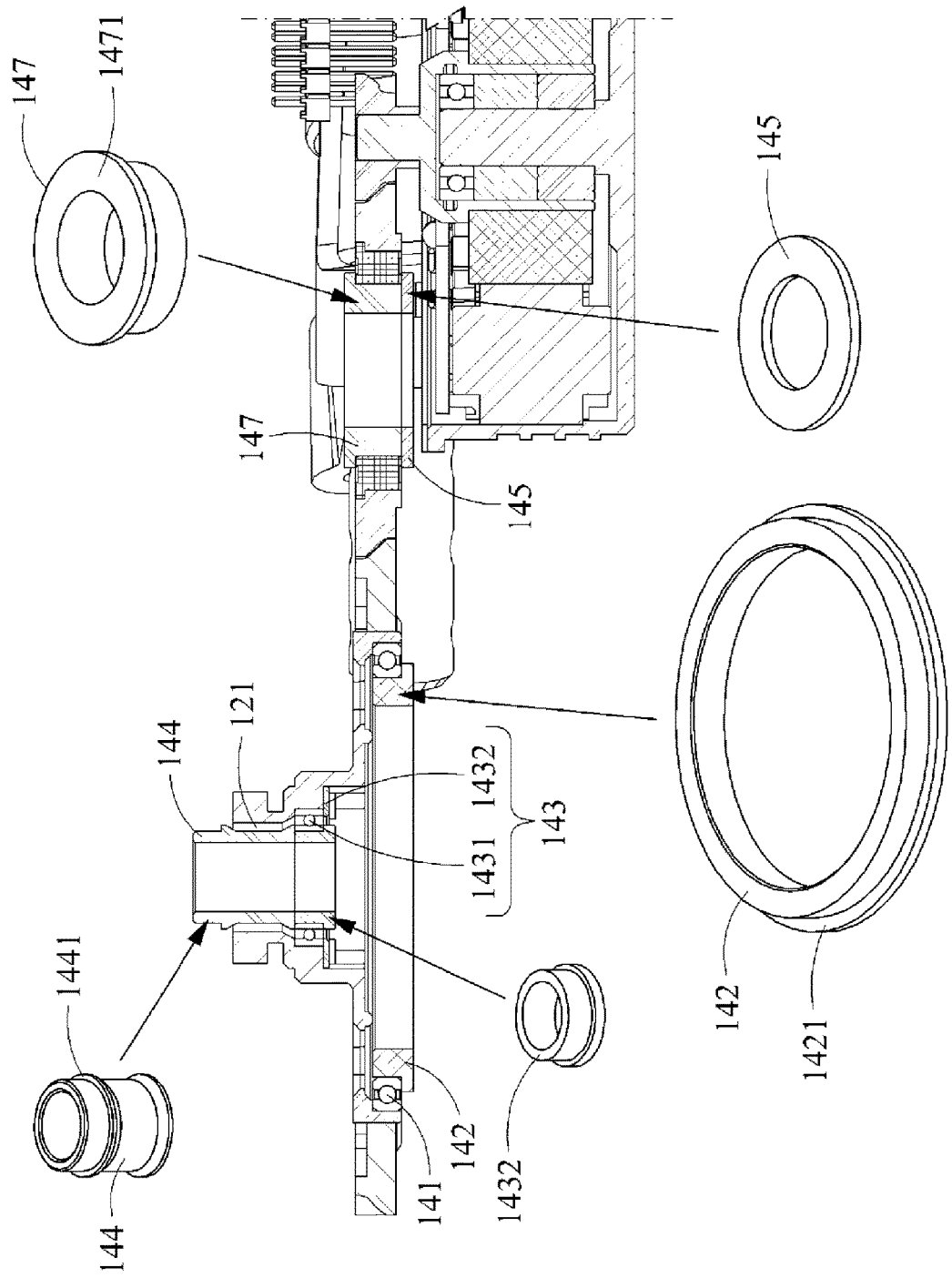
FIG. 9 is a view illustrating rings disposed in a frame set of a driving module according to at least one example embodiment.

FIG. 9 illustrates a plurality of noise reducing rings disposed in the frame set to reduce noise produced when the decelerating gear set 130 rotates.

Referring to FIG. 9, the base ring 142, the base bearing 141, and the connecting plate 134 may be disposed sequentially from a center of the shaft 121 of the base gear in a lowermost cylinder portion of the shaft 121 of the base gear. In detail, the base ring 142 and the base bearing 141 may be firmly attached to the shaft 121, and the connecting plate 134 may be rotatably attached to the shaft 121 by the base bearing 141. The base ring 142 may include a bottom side protruding in a circumferential direction of the base ring 142 to support the base bearing 141 such that the base gear and the first frame 120 may not directly touch each other and be spaced apart from each other. The base ring 142 may be provided in a shape of a flange.

The auxiliary bearing assembly 143 may be disposed in a middle cylinder portion of the shaft 121 of the base gear. The auxiliary bearing assembly 143 may include an auxiliary ring 1432 and an auxiliary bearing 1431. The auxiliary ring 1432 and the auxiliary bearing 1431 may be disposed sequentially from the center of the shaft 121 of the base gear.

The sun ring 144 may be disposed in an uppermost cylinder portion of the shaft 121 of the base gear to fill the space between the sun gear 135 and the shaft 121. The sun ring 144 may include a sun edge 1441 disposed at an upper portion than a middle of the sun ring 144. The sun edge 1441 may touch an end of the sun gear 135. The sun gear 135 may touch an end of the sun edge 1441, whereby the sun gear 135 may be attached to the shaft of the base gear not to be detached in a direction of the shaft 121.

The cap ring 147 and the bottom ring 145 may be disposed on a cylindrical surface of the shaft 124 of the idle gear 132 in the first frame 120. The idle bearing 146 may be disposed between the cap ring 147 and the idle gear 132. The bottom ring 145 may be disposed under the cap ring 147 and the idle bearing 146 such that the idle gear 132 and the first frame 120 may be spaced apart from each other not to directly touch each other. The cap ring 147 and the shaft 124 in the first frame 120 may not directly touch each other, and the shaft 1511 in the second frame 151 may be inserted between the cap ring 147 and the shaft 124 in the first frame 120.

The cap ring 147 may include a cap surface 1471 extending from an upper portion of the cap ring 147 in an outer circumferential direction of the cap ring 147, and the cap surface 1471 may be disposed on the inner side of the second frame 151 and the idle bearing 146 such that the idle gear 132 and the second frame 151 may be spaced apart from each other not to directly touch each other. The cap ring 147 may be provided in a shape of a flange.

The noise reducing rings including the base ring 142, the auxiliary ring 1432, the sun ring 144, the bottom ring 145, and the cap ring 147 as described above may include a PEEK plastic material or engineering plastic material, and reduce noise produced when the decelerating gear set 130 rotates. The noise reducing rings may be referred to herein as noise reduction members.

Further, such noise reducing rings may be disposed between a shaft and an inner race of a bearing inside the inner race of the bearing which holds a ball of the bearing to prevent transmission of noise produced by the bearing to a frame set, and the bearing may be disposed not to directly touch a shaft of a gear.

Figure 10A:
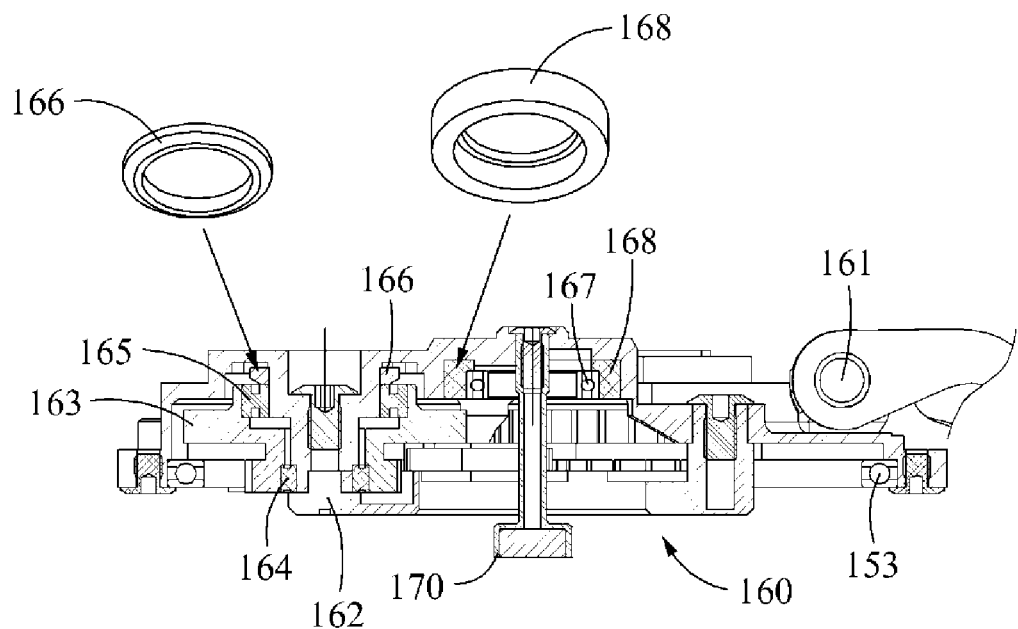
FIGS. 10A and 10B are views illustrating a rotary joint of a driving module, and rings disposed in the rotary joint according to at least one example embodiment.
Figure 10B:
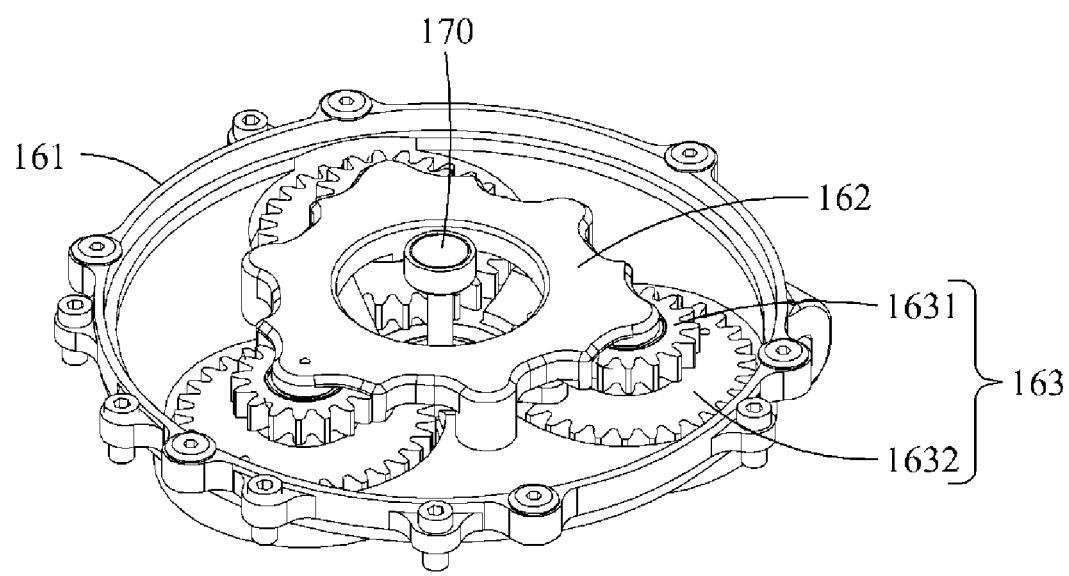

FIG. 10A is a cross-sectional view which penetrates through the center of the rotary joint 160, and FIG. 10B illustrates an arrangement of the planetary gear 163. The direction shaft 170 may be disposed at the center portion of the rotary joint 160. The direction shaft 170 may penetrate through an inner space of the shaft 121 of the first frame 120 and extend to an end of the inner side of the carrier 161.

A carrier bearing 167 and a carrier ring 168 may be disposed at a center of the carrier 161 sequentially from the center of the carrier 161 to facilitate rotation of the rotary joint 160. The sun ring 144 to be attached to the shaft 121 of the first frame 120 may be disposed in an inner space of the carrier 161. The sun gear 135 may be disposed on one side of the sun edge 1441 of the sun ring 144, and the carrier bearing 167 may be disposed on another side of the sun edge 1441 of the sun ring 144.

The planetary ring 166, the planetary bearing 165, and the batch bearing 164 may be disposed between the planetary gear 163 and a shaft of the planetary gear 163 formed in the carrier 161. An inner circumferential side of the planetary bearing 165 may touch the shaft of the planetary gear 163, and an outer circumferential side of the planetary bearing 165 may touch an inner side of the planetary gear 163. The planetary ring 166 may be disposed adjacent to the inner side of the carrier 161, and a bottom of the planetary ring 166 may touch the planetary bearing 165. The batch bearing 164 may be disposed between the planetary gear 163 and the shaft of the planetary gear 163 in the carrier 161 on an opposite side of the planetary ring 166. Thus, the planetary gear 163 may be supported by the two rings, in detail, the batch bearing 164 and the planetary ring 166, disposed on an upper side and a lower side of the rotary joint 160.

The shaft of the planetary gear 163 formed in the carrier 161 may be provided in a hollow structure, and a portion of the aligner 162 may be inserted into a hollow of the shaft of the planetary gear 163. Another portion of the aligner 162 may touch a portion of the batch bearing 164.

The aligner 162 may strengthen the rigidity of the shaft of the planetary gear 163 by connecting the shaft of the planetary gear 163 simultaneously, prevent the shaft from being bent or oscillating by force generated when the planetary gear 163 engages with the sun gear 135, and prevent a separation of the planetary gear 163 in a direction of the shaft of the planetary gear 163. To prevent bearing noise produced when a planetary gear rotates from being transmitted to a body frame, an aligner of the planetary gear may include a PEEK plastic material plastic material, whereby oscillations produced in the direction of the shaft of the planetary gear 163 may be absorbed such that gears may smoothly engage with each other, the bearing noise may be reduced, and bearing oscillation and noise may not be transmitted directly to a frame set.

Figure 11:
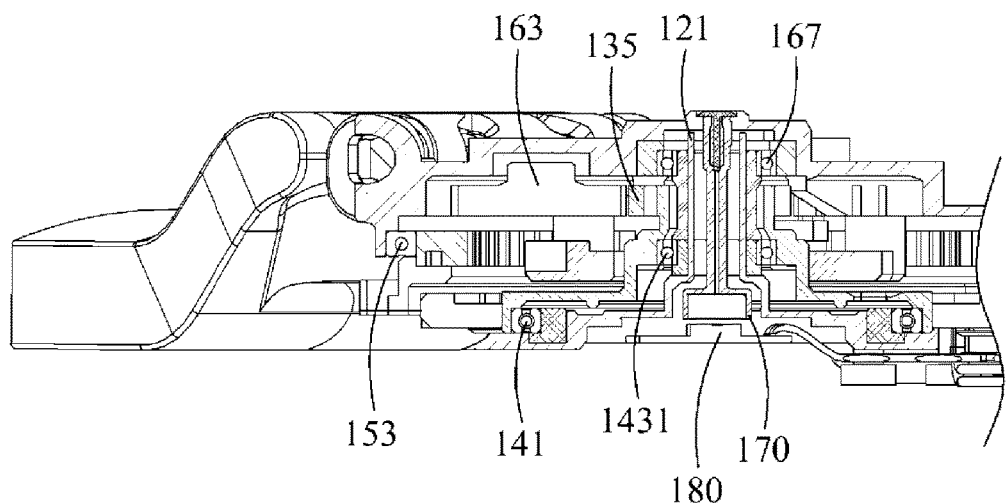
FIG. 11 is a cross-sectional view of a driving module according to at least one example embodiment.

FIG. 11 is a cross-sectional view which penetrates through a center of the driving module 100 being completely assembled.

Referring to FIG. 11, three planetary gears 163 may be disposed to form an angle of 120 degrees equally, and a portion at which the aligner 162 and the carrier 161 are coupled together may be disposed among the planetary gears 163. Among the planetary gears 163, a large-diameter gear may engage with the sun gear 135 in the carrier 161, and a size of the large-diameter gear may be determined within a range which prevents a contact between an outer side of the large-diameter gear and the inner side of the carrier 161.

When the sun gear 135 rotates, an external force may be applied to a bearing disposed in the rotary joint 160. The sun gear 135 and the three planetary gears 163 rotate simultaneously while engaging with each other and thus, forces to push the gears may be continuously applied depending on engagement positions. Accordingly, a force generated by the sun gear 135 may be transmitted to the bearing in the rotary joint 160, and the carrier 161 may receive the force in a direction perpendicular to the shaft thereof.

A slight torsion may occur by the force transmitted to the carrier 161, and the torsion may apply a force to a bearing disposed in a decelerating gear set. The decelerating gear set may rotate while being twisted by the applied force. Such a torsion may apply a non-uniform force to a surface of the bearing disposed in the decelerating gear set, and a frictional force of a bearing ball may increase. Accordingly, noise may increase and the increased noise may be transmitted to the frame set and amplified.

Thus, by configuring the sun gear 135 and the carrier 161 of the rotary joint 160 to rotate separately without being affected by rotation of each other, a planetary carrier and a joint may smoothly rotate and an increase in noise may be restrained.

A portion of the ring gear 152 may be inserted into the second frame 151, and fastened to the second frame 141 by bolts. An inner side of the joint bearing 153 may touch the outer circumferential side of the ring gear 152.

The large-diameter gear of the planetary gears 163 may engage with the sun gear 135, and simultaneously the small-diameter gear of the planetary gears 163 may engage with the ring gear 152. Thus, when the sun gear 135 rotates, the small-diameter gear of the planetary gears 163 may rotate along the circumferential surface of the ring gear 152 and whereby the carrier 161 may rotate. A rotation direction of the sun gear 135 may be opposite to a rotation direction of the small-diameter gear of the planetary gears 163.

The three bearings, in detail, the base bearing 141, the auxiliary bearing 1431, and the carrier bearing 167, may be supported around the shaft 121 of the base gear, the shaft 121 being formed integrally with the first frame 120. In an order starting from a bearing close to the first frame 120 to a bearing close to the carrier 161, the base bearing 141, the auxiliary bearing 1431, and the carrier bearing 167 may be disposed. The noise reducing rings, in detail, the base ring 142, the auxiliary ring 1432, and the carrier ring 168, formed using a PEEK plastic material or engineering plastic material may be disposed between the shaft 121 and the bearings 141, 1431, and 167, respectively.

The shaft 121 of the base gear may be provided in a hollow structure, and the direction shaft 170 may be inserted from the outer side of the first frame 120 into the shaft 121. A stopper 180 may be disposed on the outer side of the first frame 120 to prevent an escape of the direction shaft 170.

The auxiliary bearing 1431 may be disposed to be inserted into the shaft 121 of the first frame 120, rather than a shaft of the carrier 161. Thus, the base gear and the carrier 161 may rotate separately, whereby noise produced by friction at the base bearing 141 (i.e., noise produced based on interaction between the base gear and the rotary joint 160) may be at least partially mitigated. Since the base gear and the carrier 161 of the rotary joint 160 may rotate separately without being affected by rotation of each other, the rotary joint 160 may smoothly rotate and an increase in noise may be restrained.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A driving module, comprising:
a motor configured to generate power;
a gear train having first and second sides, the gear train being connected to the motor at the first side of the gear train, the gear train including,
a frame set that includes at least one frame, and
a decelerating gear set configured to rotate in response to the power generated by the motor;

a rotary joint rotatably coupled to the second side of the gear train such that the rotary joint is configured to rotate based on rotation of the decelerating gear; and a ring between the frame set and the rotary joint, the ring being configured to at least partially mitigate noise produced based on interaction between the frame set and the rotary joint if the rotary joint rotates, wherein the frame set, the decelerating gear set, and the rotary joint are serially arranged, and wherein the decelerating gear set includes, an input gear connected to a drive shaft of the motor, the input gear having a first diameter, an idle gear configured to engage with the input gear, the idle gear having a second diameter; and a base gear configured to engage with the idle gear, the base gear having a third diameter, and wherein the second diameter is greater than the first diameter according to an order of power transmission, and the third diameter is greater than the second diameter according to the order of power transmission.

2. The driving module of claim 1, wherein the gear train includes a ring gear, the decelerating gear set includes a plurality of gears, each gear of the plurality of gears including a separate shaft, and the at least one frame includes, a first frame that is integral with the separate shaft included in each gear of the plurality of gears, and a second frame coupled to the ring gear.

3. The driving module of claim 2, wherein the rotary joint includes, at least one planetary gear, the at least one planetary gear having a shaft, and a carrier that is integral with the shaft of the planetary gear, and the carrier is configured to rotate based on the planetary gear engaging with the ring gear.

4. The driving module of claim 3, wherein the base gear includes at least a first gear and a second gear, the second gear having a greater diameter than the first gear, and the first gear being configured to engage with the planetary gear.

5. The driving module of claim 4, wherein the planetary gear includes a first planetary gear and a second planetary gear, the second planetary gear having a greater diameter than the first diameter, the first planetary gear and the second planetary gear are an integral body, the first planetary gear is configured to engage with the ring gear, and the second planetary gear is configured to engage with the first gear of the base gear.

6. The driving module of claim 4, wherein the second gear of the base gear includes a high-strength plastic material, the first gear of the base gear includes a metallic material, and the first gear of the base gear is coupled to an inner side of the second gear of the base gear.

7. The driving module of claim 3, wherein the rotary joint includes an aligner configured to prevent a separation of the planetary gear, the aligner is attached to the carrier, and the planetary gear is between the rotary joint and the aligner.

8. A driving module comprising:

a motor configured to generate power;

a gear train having first and second sides, the gear train being connected to the motor at the first side of the gear train, the gear train including, a frame set that includes at least one frame, and a decelerating gear set configured to rotate in response to the power generated by the motor;

a rotary joint rotatably coupled to the second side of the gear train such that the rotary joint is configured to rotate based on rotation of the decelerating gear; and a ring between the frame set and the rotary joint, the ring being configured to at least partially mitigate noise produced based on interaction between the frame set and the rotary joint if the rotary joint rotates, wherein the frame set, the decelerating gear set, and the rotary joint are serially arranged, the gear train includes a ring gear, the decelerating gear set includes a plurality of gears, each gear of the plurality of gears including a separate shaft, the at least one frame includes, a first frame that is integral with the separate shaft included in each gear of the plurality of gears, and a second frame coupled to the ring gear, the gear train further includes a plurality of pools on at least one of an inner side of the first frame and an inner side of the second frame, and the plurality of pools are configured to at least partially mitigate noise produced by the decelerating gear set.

9. The driving module of claim 4, wherein the base gear includes a first shaft, the gear train includes a base bearing and a base ring, the base bearing and the base ring being between the base gear and the shaft of the base gear, and the base ring is spaced apart from the first frame such that the base ring is configured to isolate the base gear from the first frame.

10. The driving module of claim 9, wherein the first frame includes a second shaft the gear train includes a plurality of base bearings and a plurality of base rings, the base bearings are between the second gear of the base gear and the shaft of the first frame, and the base rings are between the first gear of the base gear and the shaft of the first frame.

11. The driving module of claim 2, wherein the gear train further includes, a bottom ring between the first frame and the idle gear, an idle bearing, and a cap ring between the second frame and a shaft of the idle gear, and the cap ring is configured to separate the idle gear from the second frame to isolate the idle gear from the second frame.

12. The driving module of claim 3, wherein the rotary joint further includes at least one planetary ring between the carrier and the planetary gear, the at least one planetary ring including a plastic material, the planetary ring being configured to at least partially mitigate noise produced based on interaction between the carrier and the planetary gear if the rotary joint rotates.

13. The driving module of claim 2, further comprising:

a magnetic direction shaft configured to extend through a shaft of the base gear and a center of the rotary joint.

14. A driving module, comprising:

a motor configured to generate power;

a decelerating gear set configured to rotate in response to the power received from the motor, the decelerating gear set including at least one spur gear;

a first frame including,
- an outer side and an inner side, the outer side being coupled to the motor, and
- a shaft of the decelerating gear set integral with the inner side, the shaft of the decelerating gear set configured to be inserted into the decelerating gear set, a second frame coupled to the inner side of the first frame;

a ring gear coupled to the second frame;

a planetary gear set configured to engage with the ring gear, the planetary gear set including at least one planetary gear;

a carrier rotatably attached to the second frame, the carrier including a shaft of the planetary gear set, the shaft of the planetary gear set configured to be inserted into the planetary gear set;

a decelerating gear bearing between the decelerating gear set and the shaft of the decelerating gear set; and a planetary gear bearing between the planetary gear set and the shaft of the planetary gear set.

15. The driving module of claim 14, wherein at least one of the first frame and the second frame includes a plurality of pools on an inner side thereof, such that the plurality of pools are configured to at least partially mitigate noise produced by the decelerating gear set, the driving module further includes,
- at least one first ring between the decelerating gear bearing and the shaft of the carrier, and
- at least one second ring between the planetary gear bearing and the carrier, and at least one of the first ring and the second ring includes a plastic material.

16. The driving module of claim 14, further comprising:

a joint bearing having an inner side and an outer side, the inner side being configured to contact the ring gear, the outer side being configured to contact the carrier, wherein the joint bearing is configured to rotatably couple the carrier to the second frame.

17. A motion assistance apparatus, comprising:

a fixing module configured to be coupled to a user;

a supporter configured to support a portion of a body of the user; and a driving module configured to drive the supporter, the driving module including,
- a motor,
- a gear train configured to receive driving power from the motor, the gear train including an output end, the gear train including a decelerating gear set configured to rotate in response to power received from the motor, the gear train including at least one frame,
- a rotary joint that includes at least one planetary gear coupled to the output end of the gear train, and
- the gear train further including a noise reduction member configured to at least partially mitigate noise produced based on interaction between the gear train and the rotary joint if the rotary joint rotates, wherein the motor, the at least one frame included in the gear train, and the rotary joint are serially arranged, and wherein the decelerating gear set includes,
- an input gear connected to a drive shaft of the motor, the input gear having a first diameter;
- an idle gear configured to engage with the input gear, the idle gear having a second diameter; and
- a base gear configured to engage with the idle gear, the base gear having a third diameter, and wherein the second diameter is greater than the first diameter according to an order of power transmission, and the third diameter is greater than the second diameter according to the order of power transmission.

18. The motion assistance apparatus of claim 17, wherein the gear train includes a planetary gear set configured to engage with the decelerating gear set and of which a shaft is in the rotary joint, and the noise reduction member includes at least one ring on a shaft of at least one of the decelerating gear set and the shaft of the planetary gear set.

19. The motion assistance apparatus of claim 18, wherein the at least one frame and the shaft of the decelerating gear are provided as an integral body, and the noise reduction member includes a plurality of pools on an inner side of the at least one frame.

* * * * *